United States Patent
Jacques et al.

(10) Patent No.: US 8,252,270 B2
(45) Date of Patent: Aug. 28, 2012

(54) COMPOSITION FOR MAKING-UP THE SKIN COMPRISING AT LEAST ONE RESIN, AT LEAST ONE BLOCK COPOLYMER AND AT LEAST ONE SOLID FATTY SUBSTANCE, FREE FROM VOLATILE OIL

(75) Inventors: Véronique Jacques, Bourg la Reine (FR); Véronique Schwartz, Chatenay Malabry (FR); Xavier Blin, Paris (FR)

(73) Assignee: L'Oreal S.A., Paris (FR)

( * ) Notice: Subject to any disclaimer, the term of this patent is extended or adjusted under 35 U.S.C. 154(b) by 445 days.

(21) Appl. No.: 12/000,936

(22) Filed: Dec. 19, 2007

(65) Prior Publication Data

US 2008/0171005 A1 Jul. 17, 2008

Related U.S. Application Data

(60) Provisional application No. 60/878,419, filed on Jan. 4, 2007, provisional application No. 60/878,420, filed on Jan. 4, 2007.

(30) Foreign Application Priority Data

Dec. 19, 2006 (FR) ...................................... 06 55650
Dec. 19, 2006 (FR) ...................................... 06 55651

(51) Int. Cl.
*A61K 8/72* (2006.01)
*A61K 31/74* (2006.01)
(52) U.S. Cl. .................. 424/70.11; 424/78.02
(58) Field of Classification Search .......................... None
See application file for complete search history.

(56) References Cited

U.S. PATENT DOCUMENTS

| 5,221,534 A | 6/1993 | DesLauriers et al. |
| 5,279,830 A * | 1/1994 | Edmundson et al. ......... 424/401 |
| 5,874,069 A | 2/1999 | Mendolia et al. |
| 5,919,441 A | 7/1999 | Mendolia et al. |
| 5,981,680 A | 11/1999 | Petroff et al. |
| 6,051,216 A | 4/2000 | Barr et al. |
| 6,303,105 B1 | 10/2001 | Shah et al. |
| 6,517,818 B1 * | 2/2003 | Golz-Berner et al. .......... 424/64 |
| 2002/0055562 A1 | 5/2002 | Butuc |
| 2004/0241121 A1 * | 12/2004 | Blin et al. ................... 424/70.11 |
| 2006/0013839 A1 * | 1/2006 | Yu ................................. 424/401 |

FOREIGN PATENT DOCUMENTS

| EP | 0 205 961 A | 12/1986 |
| EP | 0 293 795 A | 12/1988 |
| EP | 1 044 674 A | 10/2000 |
| EP | 1 086 683 A | 3/2001 |
| EP | 1 621 229 A | 2/2006 |
| EP | 1 759 690 A | 3/2007 |
| FR | 2 792 190 A | 10/2000 |

OTHER PUBLICATIONS

Handbook of Pressure Sensitive Adhesive, edited by Donatas Satas, 3rd ed., 1989, p. 609-619.
French Search Report for FR 06 55650 dated Jul. 13, 2007 (French priority application for the present application).
French Search Report for FR 06 55651 dated Jul. 13, 2007 (French priority application for the present application).

* cited by examiner

*Primary Examiner* — Brian Gulledge
(74) *Attorney, Agent, or Firm* — Oblon, Spivak, McClelland, Maier & Neustadt, L.L.P.

(57) ABSTRACT

Disclosed herein is a composition for make-up and/or care of the skin comprising a fatty phase, comprising:
   at least one resin of number average molecular weight less than or equal to 10,000 g/mol, selected from rosin, derivatives of rosin, and hydrocarbon resins,
   at least one hydrocarbon block copolymer,
   at least one fatty substance whose melting point is greater than 25° C. chosen from waxes and pasty fatty substances,
wherein said composition comprises less than 5% of volatile oil.

34 Claims, No Drawings

COMPOSITION FOR MAKING-UP THE SKIN COMPRISING AT LEAST ONE RESIN, AT LEAST ONE BLOCK COPOLYMER AND AT LEAST ONE SOLID FATTY SUBSTANCE, FREE FROM VOLATILE OIL

This application claims benefit of U.S. Provisional Application Nos. 60/878,419 and 60/878,420, filed Jan. 4, 2007, the contents of which are incorporated herein by reference. This application also claims benefit of priority under 35 U.S.C. §119 to French Patent Application Nos. FR 06 55650 and 06 55651, filed Dec. 19, 2006, the contents of which are also incorporated herein by reference.

Disclosed herein is a cosmetic composition for making-up or care of the skin, including the scalp, both the face and the human body, the lips or the integuments of human beings, such as the hair, eyelashes, eyebrows or nails, comprising a fatty phase comprising at least one resin, at least one hydrocarbon block copolymer and at least one fatty substance whose melting point is greater than 25° C. This composition can have remarkable cosmetic properties and it may endow the make-up and care product with properties of sheen and persistence of sheen after application while limiting its migration.

The composition disclosed herein can, for example, comprise a product for make-up of the body, the lips or the integuments of human beings having, for example, care and/or non-therapeutic treatment properties. It can comprise, for instance, a lipstick or lip gloss, a face or eyelid powder, a tattooing product, a mascara, an eye-liner, a nail varnish, an artificial skin tanning product, and a product for the dyeing or care of the hair.

There are many cosmetic compositions wherein the properties of sheen and comfort of the film deposited, after application onto the keratinous materials (skin, lips, integuments) may be desirable. By way of example, lipsticks, nail varnishes or again certain hair products can be cited. In addition, it may be desirable that the composition retains a good level of sheen after application. The majority of shiny compositions only, in fact, display a good level of sheen at the time of application, which diminishes rapidly after application.

In addition, compositions comprising volatile oils can have the disadvantage of leaving on the lips, after evaporation of these volatile oils, a film which very rapidly becomes uncomfortable with the passage of time (sensation of dryness, tightness and discomfort), which may deter certain people from using this type of lipstick. In addition, the deposit obtained may be matte. Often, consumers may prefer a shiny product, comfortable to wear throughout the day, which migrates little or not at all into the folds of skin surrounding the lips or the eyes such as wrinkles and minor wrinkles.

The present disclosure, thus, provides a novel method of formulating a cosmetic product which makes it possible to obtain good sheen properties at the time of application and after application while maintaining a low migration level.

The inventors have surprisingly found that by combining, in a cosmetic composition for make-up or care of the skin, at least one particular resin, at least one hydrocarbon block polymer and at least one fatty substance whose melting point is greater than 25° C., such as a wax or a pasty fatty substance in the absence of a volatile oil (or in the presence of a small quantity of volatile oil), it can be possible to create a make-up product displaying a good level of sheen at the time of application and after application.

Thus, disclosed herein is a cosmetic composition for make-up or care of the skin comprising a fatty phase comprising:

- at least one resin of number average molecular weight less than or equal to 10,000 g/mol chosen from rosin, derivatives of rosin, and hydrocarbon resins,
- at least one hydrocarbon block copolymer,
- at least one fatty substance whose melting point is greater than 25° C. chosen from waxes and pasty fatty substances, the composition comprising less than 5% by weight of volatile oil relative to the total weight of the composition, for example less than 2% by weight, or no volatile oil.

According to one embodiment, the composition comprises at least one wax and at least one pasty fatty substance, wherein the at least one fatty substance has a melting temperature greater than 25° C.

In one embodiment, the composition disclosed herein is anhydrous. As used herein, "anhydrous" means comprising less than 10% by weight of water relative to the total weight of the composition, for example less than 4%, or such as totally free from water.

In one embodiment, the composition comprises a silicone compound in an amount less than 10% relative to the total weight of the composition, for example less than 4%, or for example it comprises no silicone compound.

According to one embodiment, the composition is in liquid form at ambient temperature (25° C.).

According to another embodiment, the composition is in solid form at ambient temperature 25° C.).

In one embodiment, when the composition is in solid form, it displays a hardness greater than 30 g, for example greater than 60 g.

Measurement of Hardness

To determine the hardness of the solid composition, a stick of the composition having a circular cross section 12.7 mm in diameter is prepared. The stick is cast 24 hours before making the measurement and it is stored at a temperature of 20° C.

The hardness can be measured by the method described as the "butter-cutting knife method", which comprises cutting the stick transversely by means of a rigid tungsten wire of 250 μm diameter, moving the wire forward relative to the stick at a speed of 100 mm/min. The hardness corresponds to the maximal shear force exerted by the wire on the stick at 20° C., this force being measured by means of a DFGS2 dynamometer marketed by Indelco-Chatillon. The hardness is expressed in grams.

In one embodiment, the composition disclosed herein may display decreased stickiness.

Also disclosed herein is a non-therapeutic process for making-up or caring for the skin comprising applying to the skin a composition as defined above.

Also disclosed herein is a method of using a composition as defined above to obtain a deposit, such as make-up, on the skin making it possible to give satisfaction in terms of sheen while maintaining migration at a low level.

Resin

In one embodiment, the at least one resin used in the composition according to the disclosure has a number average molecular weight less than or equal to 10,000 g/mol, for example ranging from 250 to 10,000 g/mol, or for example less than or equal to 5,000 g/mol, or for example ranging from 250 to 5,000 g/mol, or for example less than or equal to 2,000 g/mol, or for example ranging from 250 to 2,000 g/mol, or for example less than or equal to 1,000 g/mol, or for example ranging from 250 to 1,000 g/mol.

The number average molecular weights (Mn) may be determined by liquid gel permeation chromatography (solvent THF, calibration curve established with linear polystyrene standards, refractometric detector).

In one embodiment, the at least one resin of the composition according to the disclosure is a so-called tackifying resin. Such resins are described in the Handbook of Pressure Sensitive Adhesive, edited by Donatas Satas, 3rd ed., 1989, p. 609-619.

The at least one resin of the composition according to the disclosure is chosen from rosin, derivatives of rosin, and hydrocarbon resins.

Rosin is a mixture mainly comprising organic acids called rosin acids (mainly acids of the abietic type and pimaric type). There are three types of rosin: rosin ("gum rosin") obtained by incision on live trees, wood rosin which is extracted from pine logs or wood, and tall oil ("tall oil rosin") which is obtained from a by-product deriving from the production of paper.

In one embodiment, derivatives of rosin can, for example be derived from polymerization, hydrogenation and/or esterification (for example with polyhydric alcohols such as ethylene glycol, glycerol or pentaerythritol) of rosin acids. Examples include, but are not limited to, the rosin esters marketed under the name Foral 85, Pentalyn H and Staybelite Ester 10 by Hercules; Sylvatac 95 and Zonester 85 by Arizona Chemical or Unirez 3013 by Union Camp.

In at least one embodiment, hydrocarbon resins are chosen from polymers of low molecular weight which can be classified, depending on the type of monomer which they contain, into:

indene hydrocarbon resins such as the resins derived from the polymerization of indene monomer in the greater proportion and a monomer selected from styrene, methylindene, methylstyrene and mixtures thereof in the lesser proportion. These resins may possibly be hydrogenated, and in one embodiment these resins can display a molecular weight ranging from 290 to 1150 g/mol.

As non-limiting examples of indene hydrocarbon resins, those marketed under the name Escorez 7105 by Exxon Chem., Nevchem 100 and Nevex 100 by Neville Chem., Norsolene S105 by Sartomer, Picco 6100 by Hercules and Resinall by Resinall Corp., or the hydrogenated indene/methylstyrene/styrene copolymers marketed under the name "Regalite" by Eastman Chemical, such as Regalite R 1100, Regalite R 1090, Regalite R-7100, Regalite R1010 Hydrocarbon Resin and Regalite R1125 Hydrocarbon Resin can be cited.

aliphatic pentadiene resins such as that derived from the polymerization mainly of 1,3-pentanediene (trans or cis piperylene) and a minor monomer selected from isoprene, butene, 2-methyl-2-butene, pentene, 1,4-pentadiene and mixtures thereof. In one embodiment, these resins can display a molecular weight ranging from 1,000 to 2,500 g/mol.

Such 1,3-pentadiene resins are for example marketed under the names Piccotac 95 by Eastman Chemical, Escorez 1304 by Exxon Chemicals, Nevtac 100 by Neville Chem. or Wingtack 95 by Goodyear.

mixed pentadiene and indene resins, which are derived from the polymerization of a mixture of pentadiene and indene monomers such as those described above, such as for example the resins marketed under the name Escorez 2101 by Exxon Chemicals, Nevpene 9500 by Neville Chem., Hercotac 1148 by Hercules, Norsolene A 100 by Sartomer and Wingtack 86, Wingtack Extra and Wingtack Plus by Goodyear.

diene resins from cyclopentadiene dimers, such as those derived from the polymerization of a first monomer selected from indene and styrene, and a second monomer selected from dimers of cyclopentadiene such as dicyclopentadiene, methyldicyclopentadiene, other dimers of pentadiene, and mixtures thereof. These resins generally display a molecular weight ranging from 500 to 800 g/mol, such as for example those marketed under the name Betaprene BR 100 by Arizona Chemical Co., Neville LX-685-125 and Neville LX-1000 by Neville Chem., Piccodiene 2215 by Hercules, Petro-Rez 200 by Lawter or Resinall 760 by Resinall Corp.

diene resins from isoprene dimers such as the terpene resins derived from the polymerization of at least one monomer selected from α-pinene, β-pinene, limonene, and mixtures thereof. In one embodiment, these resins can display a molecular weight ranging from 300 to 2,000 g/mol. Such resins are for example marketed under the name Piccolyte A115 and S125 by Hercules and Zonarez 7100 or Zonatac 105 Lite by Arizona Chem.

Certain modified resins useful herein, such as hydrogenated resins include those marketed under the name Eastotac C6-C20 Polyolefin by Eastman Chemical Co., under the name Escorez 5300 by Exxon Chemicals or the resins Nevillac Hard or Nevroz offered by Neville Chem., the resins Piccofyn A-100, Piccotex 100 or Piccovar AP25 offered by Hercules or the resin SP-553 offered by Schenectady Chemical Co.

According to one embodiment, the at least one resin is selected from hydrocarbon indene resins, such as the hydrogenated indene/methylstyrene/styrene copolymers marketed under the name "Regalite" by Eastman Chemical, such as Regalite R 1100, Regalite R 1090, Regalite R-7100, Regalite R1010 Hydrocarbon Resin and Regalite R1125 Hydrocarbon Resin.

In one embodiment, the at least one resin can be present in the composition according to the present disclosure in an amount ranging from 0.1 to 30% by weight, relative to the total weight of the composition, for example ranging from 0.3 to 20% by weight, or for example from 0.5 to 15% by weight.

Hydrocarbon Block Copolymer

According to one embodiment, the composition can contain, apart from the at least one resin, at least one hydrocarbon block copolymer also referred to as block copolymer, such as a block copolymer soluble or dispersible in a liquid fatty phase as defined above.

In another embodiment, the at least one hydrocarbon block copolymer is chosen from diblocks, triblocks, multiblocks, and radial and star copolymers. Such hydrocarbon block copolymers are described, for example, in U.S. Patent Application Publication No. 2002/005562 and in U.S. Pat. No. 5,221,534.

In one embodiment, the at least one block copolymer can display at least one block wherein the glass transition temperature is lower than 20° C., for example less than or equal to 0° C., or for example less than or equal to −20° C., or for example less than or equal to −40° C. In another embodiment, the glass transition temperature of the at least one block can range from −150° C. to 20° C., for example from −100° C. to 0° C.

In this case, when the at least one resin is endowed with at least one glass transition temperature, the divergence between the glass transition temperatures of the at least one resin and the copolymer is generally greater than 20° C., for example greater than 40° C., or for example greater than 60° C.

When the at least one resin is endowed with at least one glass transition temperature, the block copolymer may be a plasticizer of the at least one resin previously described. As used herein, "plasticizer of the resin" is means a compound which, when combined in sufficient quantity with the at least one resin, lowers the glass transition temperature of the at least one resin as defined above. In one embodiment, the plasticizing compound lowers the glass transition temperature of the polymer by at least 2° C., such as by 3 or 4° C., or for example by an amount ranging from 5° C. to 20° C.

In one embodiment, the at least one hydrocarbon block copolymer present in the composition according to the disclosure is an amorphous copolymer formed by polymerization of an olefin. In one embodiment, the olefin can be an ethylenically unsaturated elastomer monomer.

As examples of olefins mention may be made of, ethylenic carbide monomers, for example those comprising one or two ethylenic unsaturations, comprising from 2 to 5 carbon atoms, such as ethylene, propylene, butadiene, isoprene or pentadiene.

In one embodiment, the at least one hydrocarbon block copolymer is an amorphous block copolymer of styrene and olefin.

In one embodiment, the at least one block copolymer comprises at least one styrene block and at least one block containing units chosen from butadiene, ethylene, propylene, butylene, isoprene and mixtures thereof.

According to one embodiment, the at least one hydrocarbon block copolymer is hydrogenated to reduce the residual ethylenic unsaturations after the polymerization of the monomers.

In another embodiment, the at least one hydrocarbon block copolymer is a copolymer, which may be hydrogenated, comprising styrene blocks and $C_3$-$C_4$ ethylene/alkylene blocks.

As diblock copolymers, which may be hydrogenated, non-limiting mention may be made of styrene-ethylene/propylene copolymers, styrene-ethylene/butadiene copolymers and styrene-ethylene/butylene copolymers. For example, diblock polymers are sold under the name Kraton® G1701E by Kraton Polymers.

As triblock copolymers, which may be hydrogenated, non-limiting mention may be made of styrene-ethylene/propylene-styrene copolymers, styrene-ethylene/butadiene-styrene copolymers, styrene-ethylene/butylene-styrene copolymers, styrene-isoprene-styrene copolymers and styrene-butadiene-styrene copolymers. For example, triblock polymers are sold under the names Kraton ® G1650, Kraton ® G1652, Kraton ® D1101, Kraton® D 1102, Kraton® D 1160 by Kraton Polymers.

In one embodiment, the at least one hydrocarbon block copolymer is a styrene-ethylene/butylene-styrene triblock copolymer.

In one embodiment, a mixture of a styrene-butylene/ethylene-styrene triblock copolymer and a styrene-ethylene/butylene diblock copolymer, such as those sold under the name Kraton® G1657M by Kraton Polymers, can be used.

In one embodiment, the at least one resin is selected from the hydrogenated indene/methylstyrene/styrene copolymers.

In one embodiment, the ratio by weight of the at least one resin to the at least one hydrocarbon block copolymer ranges from 1/1 to 4/1.

In another embodiment, the ratio by weight of the at least one resin to the at least one hydrocarbon block copolymer ranges from 1/1 to 3.5/1.

In another embodiment, the at least one hydrocarbon block copolymer can be present in a total amount ranging from 0.1% to 15% by weight, relative to the total weight of the composition, for example ranging from 0.5% to 10% by weight, or for example ranging from 1% to 8% by weight.

Fatty Phase

In at least one embodiment, the fatty phase of the composition according to the disclosure comprises at least one fatty substance whose melting point is greater than 25° C., chosen from waxes and pasty fatty substances.

As used herein, the melting point corresponds to the temperature of the most endothermic peak observed in thermal analysis (DSC) as described in the standard ISO 11357-3; 1999. The melting point of a pasty substance or a wax can be measured by means of a differential scanning calorimeter (DSC), for example the calorimeter sold under the name "MDSC 2920" by TA Instruments.

The measurement protocol is as follows:

A sample of 5 mg of paste or of wax (depending on the case) placed in a crucible is subjected to a first temperature increase passing from −20° C. to 100° C., at a heating rate of 10° C./minute, then is cooled from 100° C. to −20° C. at a cooling rate of 10° C./minute and finally subjected to a second temperature increase passing from −20° C. to 100° C. at a heating rate of 5° C./minute. During the second temperature increase, the variation in the difference between the power absorbed by the empty crucible and the crucible containing the sample of wax as a function of the temperature is measured. The melting point of the compound is the temperature value corresponding to the top of the peak of the curve representing the variation in the difference in power absorbed as a function of the temperature.

Pasty Substances

As used herein, "pasty substance" means a lipophilic fatty compound at reversible solid/liquid change of state, displaying an anisotropic crystalline organization in the solid state, and comprising a liquid fraction and a solid fraction at a temperature of 23° C.

In one embodiment, the initial melting point of the at least one pasty substance can be less than 23° C. In one embodiment, the liquid fraction of the at least one pasty substance can be present in an amount ranging from 9 to 97% relative to the total weight of the compound as measured at 23° C. In a further embodiment, the liquid fraction is present in an amount ranging from 15 to 85% relative to the total weight of the composition at 23° C., for example from 40 to 85%.

In at least one embodiment, the liquid fraction by weight of the at least one pasty substance at 23° C. is equal to the ratio of the enthalpy of fusion consumed at 23° C. to the enthalpy of fusion of the pasty substance.

As used herein, "enthalpy of fusion of the pasty substance" means the enthalpy consumed by the compound in order to pass from the solid state to the liquid state. The at least one pasty substance is said to be in the solid state when the whole of its mass is in crystalline solid form. The at least one pasty substance is said to be in the liquid state when the whole of its mass is in liquid form.

The enthalpy of fusion of the at least one pasty substance is equal to the area under the curve of the thermogram obtained by means of a differential scanning calorimeter (DSC) such as the calorimeter sold under the name MDSC 2920 by TA instruments, with a temperature increase of 5 or 10° C. per minute, in accordance with the standard ISO 11357-3:1999. The enthalpy of fusion of the at least one pasty substance is also a measure of the quantity of energy necessary to make the compound pass from the solid state to the liquid state. It is expressed in J/g.

The enthalpy of fusion consumed at 23° C. is the quantity of energy absorbed by the sample in order to pass from the solid state to the state which it displays at 23° C., comprising a liquid fraction and a solid fraction.

In one embodiment, the liquid fraction of the at least one pasty substance measured at 32° C. is present in an amount ranging from 30 to 100% relative to the weight of the compound, for example from 50 to 100% or from 60 to 100% relative to the weight of the compound. In one embodiment, wherein the liquid fraction of the at least one pasty substance measured at 32° C. is equal to 100%, the temperature of the end of the melting range of the at least one pasty substance is less than or equal to 32° C.

In one embodiment, the liquid fraction of the at least one pasty substance measured at 32° C. is equal to the ratio of the enthalpy of fusion consumed at 32° C. to the enthalpy of fusion of the at least one pasty substance. The enthalpy of fusion consumed at 32° C. is calculated in the same way as the enthalpy of fusion consumed at 23° C.

In one embodiment, the at least one pasty substance can have a hardness at 20° C. ranging from 0.001 to 0.5 MPa, for example from 0.02 to 0.4 MPa.

The hardness may be measured according to a method of penetration of a probe into a sample of compound, for example via a texture analyzer (for example the TA-XT2i from Rhéo) equipped with a stainless steel cylinder of 2 mm diameter. The hardness measurement, according to the present disclosure, was performed at 20° C. at the center of 5 samples. The cylinder was introduced into each sample at a pre-velocity of 1 mm/s then at a measurement velocity of 0.1 mm/s, the penetration depth being 0.3 mm. The hardness value recorded is that of the maximum peak.

The measurement protocol is as follows:

The at least one fatty substance whose melting point is greater than 25° C. (paste or wax depending on the case) is melted at a temperature equal to the melting point of the fatty substance +10° C. The melted fatty substance is poured into a vessel of 25 mm diameter and 20 mm depth. It is recrystallized at ambient temperature (25° C.) for 24 hours in such a manner that the surface of the fatty substance is flat and smooth, then the fatty substance is kept for at least 1 hour at 20° C. before measuring the hardness or the stickiness.

The mobile probe of the texturometer is moved at a velocity of 0.1 mm/s, then penetrates into the fatty substance to a penetration depth of 0.3 mm. When the probe has penetrated into the fatty substance to the depth of 0.3 mm, the probe is kept immobile for 1 second (corresponding to the relaxation time), then is withdrawn at a velocity of 0.5 mm/s.

The hardness value is the maximal measured compression force divided by the area of the cylinder of the texturometer in contact with the fatty substance.

In one embodiment, the at least one pasty substance is chosen from synthetic compounds and compounds of plant origin. In one embodiment, the at least one pasty substance can be obtained by synthesis from starting materials of plant origin.

In one embodiment, the at least one pasty substance is chosen from lanoline and derivatives thereof;
polyol ethers chosen from ethers of pentaerythritol and a polyalkylene glycol, ethers of a fatty alcohol and a sugar, and mixtures thereof, ethers of pentaerythritol and polyethylene glycol comprising 5 ethylene oxide units (5 EO) (CTFA name: PEG-5 pentaerythrityl ether), ethers of pentaerythritol and polypropylene glycol comprising 5 propylene oxide units (5 PO) (CTFA name: PPG-5 pentaerythrityl ether), and mixtures thereof, and in a further embodiment the mixture of PEG-5 pentaerythrityl ether, PPG-5 pentaerythrityl ether and soya oil marketed under the name "Lanolide" by Vevy, and a mixture wherein the constituents are present in a 46/46/8 ratio by weight: 46% of PEG-5 pentaerythrityl ether, 46% of PPG-5 pentaerythrityl ether and 8% of soya oil;
silicone compounds whether or not polymeric;
fluorinated compounds whether or not polymeric; and
vinyl polymers, such as:
homopolymers of olefins (such as polyvinyl laurate),
copolymers of olefins,
homopolymers and copolymers of hydrogenated dienes,
linear or branched oligomers, homo- or copolymers of alkyl, (meth)acrylates, for example those comprising from $C_8$-$C_{30}$ alkyl groups,
homo oligomers and copolymers of vinyl esters comprising from $C_8$-$C_{30}$ alkyl groups,
homo oligomers and copolymers of vinyl ethers comprising from $C_8$-$C_{30}$ alkyl groups;
liposoluble polyethers resulting from polyetherification between at least one C2-C100, diol, for example at least one C2-C50 diol; and
esters.

In one embodiment, the at least one pasty substance is polymeric, for example a hydrocarbon polymer.

Examples of liposoluble polyethers include, but are not limited to, copolymers of ethylene oxide and/or propylene oxide with long-chain C6-C30 alkylene oxides, for example such that the ratio by weight of the ethylene oxide and/or propylene oxide to alkylene oxides in the copolymer ranges from 5:95 to 70:30. In this family, copolymers such as the long-chain alkylene oxides are arranged in blocks having an average molecular weight from 1,000 to 10,000, for example polyoxyethylene/polydodecyl glycol block copolymers such as the ethers of dodecanediol (22 mol) and polyethylene glycol (45 EO) marketed under the trade name Elfacos ST9 by Akzo Nobel may be used.

In one embodiment, esters, are chosen from the following:
esters of an oligomeric glycerol, for example esters of diglycerol, such as condensation products of adipic acid and glycerol, wherein some of the hydroxyl groups of the glycerols have reacted with a mixture of fatty acids such as capric acid, stearic acid and isostearic acid and 12-hydroxystearic acid, for example those marketed under the trade name Softisan 649 by Sasol,
arachidyl propionates marketed under the trade name Waxenol 801 by Alzo,
esters of phytosterol,
triglycerides of fatty acids and derivatives thereof,
esters of pentaerythritol,
non-crosslinked polyesters resulting from polycondensation between a dicarboxylic acid or a linear or branched C4-C50 polycarboxylic acid and a C2-C50 diol or polyol, and
aliphatic esters of esters resulting from the esterification of an ester of an aliphatic hydroxycarboxylic acid with an aliphatic carboxylic acid.

In at least one embodiment, the aliphatic carboxylic acid comprises from 4 to 30 carbon atoms, for example from 8 to 30 carbon atoms. In another embodiment, it is chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid, docosanoic acid, and mixtures thereof.

In at least one embodiment, the aliphatic carboxylic acid is branched.

In another embodiment, the aliphatic hydroxycarboxylic acid ester is derived from an aliphatic hydroxycarboxylic acid comprising from 2 to 40 carbon atoms, for example from 10 to 34 carbon atoms or from 12 to 28 carbon atoms, and comprising from 1 to 20 hydroxyl groups, for example from 1 to 10 hydroxyl groups or from 1 to 6 hydroxyl groups. In another embodiment, the at least one aliphatic hydroxycarboxylic acid ester is chosen from:
  a) partial or total esters of saturated, linear monohydroxylated aliphatic monocarboxylic acids;
  b) partial or total esters of unsaturated monohydroxylated aliphatic monocarboxylic acids;
  c) partial or total esters of saturated monohydroxylated aliphatic polycarboxylic acids;
  d) partial or total esters of saturated polyhydroxylated aliphatic polycarboxylic acids; and
  e) partial or total esters of $C_2$ to $C_{16}$ aliphatic polyols which have reacted with a mono- or polyhydroxylated aliphatic mono- or polycarboxylic acid, and mixtures thereof.

In one embodiment, the aliphatic ester esters are chosen from:
  esters resulting from the esterification reaction of hydrogenated castor oil with isostearic acid in the proportions 1 to 1 (1/1) or hydrogenated castor oil monoisostearate,
  esters resulting from the esterification reaction of hydrogenated castor oil with isostearic acid in the proportions 1 to 2 (1/2) or hydrogenated castor oil diisostearate,
  esters resulting from the esterification reaction of hydrogenated castor oil with isostearic acid in the proportions 1 to 3 (1/3) or hydrogenated castor oil triisostearate,
  and mixtures thereof.

In one embodiment, the at least one pasty substance is present in an amount ranging from 0.1 to 80% relative to the weight of the composition, for example from 0.5 to 60%, or for example from 1 to 30%, or for example from 1 to 15% relative to the weight of the composition.

Waxes

The at least one wax used in the context of the present disclosure is generally a lipophilic compound, solid at ambient temperature (25° C.), deformable or non-deformable, with a reversible solid/liquid change of state, having a melting point greater than or equal to 30° C. which can range up to 200° C., for example up to 120° C.

In one embodiment, by bringing the at least one wax into the liquid state (melting), it is possible to make it miscible with oils and to form a macroscopically homogeneous mixture, but on returning the temperature of the mixture to the ambient temperature, a crystallisation of the at least one wax in the oils of the mixture is obtained. In one embodiment, the waxes suitable for the disclosure can display a melting point greater than or equal to 45° C., for example greater than or equal to 55° C.

Examples of waxes which can be used according to the disclosure include, but are not limited to:
  waxes of animal origin such as beeswax, spermaceti, lanolin wax and derivatives of lanolin, plant waxes such as Carnauba, Candellila, Ouricury, Japan, and cocoa butter wax, or cork fiber or sugar-cane waxes,
  inorganic waxes, for example paraffin, vaseline or lignite waxes or microcrystalline waxes or ozokerites,
  synthetic waxes including polyethylene waxes and waxes obtained by Fisher-Tropsch synthesis,
  silicone waxes, such as substituted linear polysiloxanes; for example silicone polyether waxes, alkyl or alkoxydimethicones comprising from 16 to 45 carbon atoms and alkyl methicones such as the $C_{30}$-$C_{45}$ alkyl methicone sold under the trade name "AMS C 30" by Dow Corning,
  hydrogenated oils set at 25° C. such as hydrogenated castor oil, hydrogenated jojoba oil, hydrogenated palm oil, hydrogenated tallow, hydrogenated coconut oil and fatty acids set at 25° C. such as the $C_{20}$-$C_{40}$ alkyl stearate sold under the trade name "Kester Wax K82H" by Koster Keunen,
  and/or mixtures thereof.

In one embodiment, the at least one wax is chosen from polyethylene waxes, microcrystallines waxes, carnauba waxes, hydrogenated jojoba oil, candellila waxes, and beeswaxes.

Waxes which can be used in the compositions according to the disclosure generally display a hardness ranging from 0.01 MPa to 15 MPa, for example greater than 0.05 MPa, and greater than 0.1 MPa.

The hardness is determined by measurement of the compression force measured at 20° C. via the texturometer sold under the name TA-XT2i by Rhéo, equipped with a stainless steel cylinder of 2 mm diameter moving at a measurement velocity of 0.1 mm/s, and penetrating into the wax to a penetration depth of 0.3 mm.

The measurement protocol is as follows:

The wax is melted at a temperature equal to the melting point of the wax +10° C. The melted wax is poured into a vessel of 25 mm diameter and 20 mm depth. The wax is recrystallized at ambient temperature (25° C.) for 24 hours in such a manner that the surface of the wax is flat and smooth, then the wax is kept for at least 1 hour at 20° C. before measuring the hardness or the stickiness.

The mobile probe of the texturometer is moved at a velocity of 0.1 mm/s, then penetrates into the wax to a penetration depth of 0.3 mm. When the probe has penetrated into the wax to the depth of 0.3 mm, the probe is kept immobile for 1 second (corresponding to the relaxation time), then is withdrawn at a velocity of 0.5 mm/s.

As used herein, "hardness value" means the maximal measured compression force divided by the area of the cylinder of the texturometer in contact with the wax.

Further examples of waxes suitable for the present disclosure include, but are not limited to, hydrocarbon waxes such as beeswax, lanoline wax, and Chinese insect waxes, rice bran wax, Carnauba wax, Candellila wax, Ouricury wax, Alfa wax, berry wax, shellac wax, Japan wax and sumac wax; montan wax, orange and lemon waxes, microcrystalline waxes, paraffins and ozokerite; polyethylene waxes, waxes obtained by the Fisher-Tropsch synthesis and waxy copolymers and esters thereof.

In one embodiment, at least one wax is obtained by catalytic hydrogenation of animal or plant oils having linear or branched $C_8$-$C_{32}$ fatty chains. Examples of these waxes include, but are not limited to, isomerized jojoba oil such as the trans isomerized partially hydrogenated jojoba oil produced or marketed by Desert Whale under the trade name Iso-Jojoba-50®, hydrogenated sunflower oil, hydrogenated castor oil, hydrogenated copra oil, hydrogenated lanolin oil and the di-(1,1,1-trimethylolpropane) tetrastearate sold under the name Hest 2T-4S® by Heterene.

In one embodiment, silicone waxes and fluorinated waxes can also be used.

In another embodiment, the waxes obtained by hydrogenation of castor oil esterified with cetyl alcohol, such as those sold under the names Phytowax ricin 16L64® and 22L73® by Sophim can also be used. Non-limiting examples of such waxes are described in French Patent Application No. FR-A-2792190.

In another embodiment, the at least one wax comprises a $C_{20}$-$C_{40}$ alkyl (hydroxystearyloxy)stearate (the alkyl group comprising from 20 to 40 carbon atoms), alone or in a mixture.

In a further embodiment, the at least one wax is chosen from those sold under the names "Kester Wax K 82 P®" and "Kester Wax K 80 P®" by Koster Keunen.

In one embodiment, the composition according to the disclosure can comprise at least one wax and/or at least one pasty fatty substance whose melting point is greater than 25° C. in an amount ranging from 0.1 to 20% by weight relative to the total weight of the composition, for example in an amount ranging from 0.5 to 15% or from 1 to 12%.

In one embodiment, the at least one fatty substance can be chosen in a varied manner by the person skilled in the art so as to prepare a composition having the desired properties, for example as regards consistency or texture.

In one embodiment, the fatty phase of the composition according to the disclosure can also comprise at least one fatty substance other than the waxes or the pasty fatty substances cited above, such as nonvolatile oils.

In one embodiment, the composition comprises at least one nonvolatile oil.

As used herein, "nonvolatile oil" means an oil remaining on the skin at ambient temperature and atmospheric pressure for at least several hours and having a vapor pressure lower than 0.13 Pa (0.01 mm Hg).

In one embodiment, the at least one nonvolatile oil is chosen from hydrocarbon oils, such as of animal or plant origin, silicone oils, or mixtures thereof. As used herein, "hydrocarbon oil" means an oil comprising mainly hydrogen and carbon atoms, and optionally oxygen, nitrogen, sulphur and/or phosphorus atoms.

In another embodiment, the at least one nonvolatile oil can be chosen from nonvolatile fluorinated hydrocarbon oils and/or silicone oils.

In one embodiment, the at least one nonvolatile hydrocarbon oil is chosen from:

hydrocarbon oils of animal origin;

hydrocarbon oils of plant origin such as the triglycerides comprising esters of fatty acids and glycerol, wherein the fatty acids can have chain lengths varying from $C_4$ to $C_{24}$, and the latter can be linear or branched, saturated or unsaturated; for example triglycerides of heptanoic acid or octanoic acid, or else wheat germ, sunflower, grape seed, sesame, maize, apricot, castor, shea, avocado, olive, soya, sweet almond, palm, rape, cotton, hazelnut, macadamia, jojoba, lucerne, poppy, Chinese okra, sesame, marrow, blackcurrant, evening primrose, millet, barley, quinoa, rye, safflower, candlenut, passionflower or muscat rose oils; shea butter; or triglycerides of caprylic/capric acids such as those sold by Stearineries Dubois or those sold under the names Miglyol 810®, 812® and 818® by Dynamit Nobel;

synthetic esters comprising from 10 to 40 carbon atoms;

linear or branched hydrocarbons of inorganic or synthetic origin such as vaseline, polydecenes, hydrogenated polyisobutene such as Parleam®, squalane, paraffin oils, and mixtures thereof;

synthetic esters such as the oils of formula $R_1COOR_2$ wherein $R_1$ represents the residue of a linear or branched fatty acid comprising from 1 to 40 carbon atoms and $R_2$ represents a hydrocarbon chain, for example a branched chain, comprising from 1 to 40 carbon atoms provided that $R_1+R_2$ is $\geq 10$, such as for example Purcellin oil (cetostearyl octanoate), isopropyl myristate, isopropyl palmitate, benzoates of $C_{12}$ to $C_{15}$ alcohols, hexyl laurate, diisopropyl adipate, isononyl isononanoate, isodecyl neopentanoate, 2-ethylhexyl palmitate, isostearyl isostearate, 2-hexyldecyl laurate, 2-octyldecyl palmitate, 2-octyldodecyl myristate, heptanoates, octanoates, decanoates or ricinoleates of alcohols or polyalcohols such as propylene glycol dioctanoate; hydroxylated esters such as isostearyl lactate, isostearyl malate or 2-octyldodecyl lactate; polyol esters and pentaerythritol esters;

branched carbon chain and/or unsaturated fatty alcohols liquid at ambient temperature comprising from 12 to 26 carbon atoms, such as octyldodecanol, isostearyl alcohol, oleyl alcohol, 2-hexyldecanol, 2-butyloctanol, and 2-undecylpentadecanol;

higher fatty acids such as the oleic acid, linoleic acid, linolenic acid; and mixtures thereof.

In another embodiment, at least one nonvolatile silicone oil is chosen from nonvolatile polydimethylsiloxanes (PDMS), polydimethylsiloxanes containing alkyl or alkoxy side groups within or at the ends of silicone chains, the groups each comprising from 2 to 24 carbon atoms, phenylated silicones such as phenyl trimethicones, phenyl dimethicones, phenyl trimethylsiloxy diphenylsiloxanes, diphenyl dimethicones, diphenyl methyldiphenyl trisiloxanes, and mixtures thereof.

In one embodiment, the at least one nonvolatile oil can be present in the composition in an amount ranging from 10 to 90% by weight, relative to the total weight of the composition, for example ranging from 10 to 80% by weight.

In one embodiment, the fatty phase can be present in the composition in an amount ranging from 10% to 95% by weight, relative to the total weight of the composition, for example ranging from 15% to 85% by weight, or for example ranging from 20% to 80% by weight.

In at least one embodiment, the composition disclosed herein is free from volatile oil. In another embodiment the composition comprises less than 5% volatile oil by weight relative to the total weight of the composition, for example less than 2% thereof, this then being present only in the state of "traces."

As used herein, "volatile oil" means any oil capable of evaporation on contact with the skin, at ambient temperature and atmospheric pressure. In one embodiment, the volatile oils disclosed herein are volatile cosmetic oils, liquid at ambient temperature, having a non-zero vapor pressure at ambient temperature and atmospheric pressure, for example ranging from 0.13 Pa to 40,000 Pa (0.001 to 300 mm Hg) or ranging from 1.3 to 1300 Pa (0.01 to 10 mm Hg).

Thickening Agent of Additional Oils:

In one embodiment, the composition disclosed herein can further comprise, at least one thickening agent of oils chosen from polymeric thickening agents and inorganic thickening agents.

In one embodiment, the at least one polymeric thickening agent of oils present in the composition disclosed herein can be an amorphous polymer formed by polymerization of an olefin. In a further embodiment, the olefin can be an ethylenically unsaturated elastomer monomer.

Examples of olefins include, but are not limited to, ethylenic carbide monomers, for example those comprising one or two ethylenic unsaturations, comprising from 2 to 5 carbon atoms, such as ethylene, propylene, butadiene, or isoprene.

In at least one embodiment, the at least one polymeric thickening agent of oils is capable of thickening or gelling the organic phase of the composition. As used herein, "amorphous polymer" means a polymer which does not have a crystalline form. In another embodiment, the at least one polymeric thickening agent can also be filmogenic, in other words it can form a film when it is applied onto the skin.

In another embodiment, the at least one polymeric thickening agent of oils can be chosen from:
- polycondensation products of the polyamide type resulting from condensation between (α) at least one acid chosen from dicarboxylic acids comprising at least 32 carbon atoms, such as the dimeric fatty acids and (β) alkylenediamines, such as ethylenediamine, wherein the polymeric polyamide comprises at least one terminal carboxylic acid group esterified or amidated with at least one monoalcohol or one monoamine comprising from 12 to 30 linear and saturated carbon atoms, for example ethylenediamine/stearyl dilinoleate copolymers such as that marketed under the name Uniclear 100 VG® by Arizona Chemical; and
- silicone polymers of the following types:
  1) polyorganosiloxanes comprising at least two groups capable of entering into hydrogen interactions, wherein these two groups are situated in the polymer chain, and/or.
  2) polyorganosiloxanes comprising at least two groups capable of entering into hydrogen interactions, wherein these two groups are situated on grafts or branches.

In a further embodiment, the at least two groups capable of entering into hydrogen interactions are chosen from from ester, amide, sulphonamide, carbamate, thiocarbamate, urea, urethane, thiourea, oxamido, guanidino and biguanidino groups.

In at least one one embodiment, the at least one silicone polymer used as structuring agents in the composition are polymers of the polyorganosiloxane type, such as for example those described in U.S. Pat. Nos. 5,874,069, 5,919,441, 6,051,216 and 5,981,680.

In another embodiment, the composition disclosed herein can also comprise at least one inorganic thickening agent of oils, such as at least one organophilic clay or at least one pyrogenic silica.

As used herein, "organophilic clays" mean clays modified with chemical compounds rendering the clay capable of swelling in oily media.

The clays are products already well known in themselves, which are for example described in the book "Mineralogy of clays, S. Caillère, S. Hénin, M. Rautureau, 2nd edition 1982, Masson", the teaching of which is incorporated herein by reference in its entirety.

In one embodiment, the at least one clay is a silicate comprising a cation which may be chosen from the cations of calcium, magnesium, aluminium, sodium, potassium, and lithium.

Examples of such clays include, but are not limited to, the clays of the smectite family such as montmorillonites, hectorites, bentonites, beidellites, saponites, and the vermiculite family, stevensite, and chlorites.

These clays can be of natural or synthetic origin. In one embodiment, clays which are cosmetically compatible and acceptable with keratinous materials, such as the skin, are used.

In one embodiment, the at least one organophilic clay is chosen from montmorillonite, bentonite, hectorite, attapulgite, and sepiolite. In a further embodiment, the clay is a bentonite or a hectorite.

In another embodiment, the at least one clay can be modified with at least one chemical compound chosen from qua- ternary amines, tertiary amines, amine acetates, imidazolines, amine soaps, fatty sulphates, alkyl aryl sulphonates, and amine oxides.

In another embodiment, the at least one organophilic clay is chosen from the quaternium-18 bentonites such as those sold under the names Bentone 3, Bentone 38 and Bentone 38V by Rheox, Tixogel VP by United catalyst and Claytone 34, Claytone 40 and Claytone XL by Southern Clay; stearalkonium bentonites such as those sold under the names Bentone 27 by Rheox, Tixogel LG by United Catalyst and Claytone AF and Claytone APA by Southern Clay; and the quaternium-18/benzalkonium bentonites such as those sold under the names Claytone HT and Claytone PS by Southern Clay.

In one embodiment, the at least one pyrogenic silica can be obtained by high temperature hydrolysis of a volatile compound of silicone in an oxyhydrogen flame, producing a finely divided silica. In another embodiment, this process may make it possible to obtain hydrophilic silicas which display a considerable number of silanol groups on their surface. Examples of such hydrophilic silicas include, but are not limited to, those marketed under the names "Aerosil 130®", "Aerosil 200®", "Aerosil 255®", "Aerosil 300®" and "Aerosil 380®" by Degussa, and "Cab-O-Sil HS-5®", "Cab-O-Sil EH-5®", "Cab-O-Sil LM-130®", "Cab-O-Sil MS-55®" and "Cab-O-Sil M-5®" by Cabot.

It is possible to modify the surface of the silica chemically, by a chemical reaction resulting in a decrease in the number of silanol groups. In one embodiment, silanol groups can be replaced by hydrophobic groups; a hydrophobic silica is then obtained.

In one embodiment, the at least one hydrophobic group is chosen from:
- trimethylsiloxyl groups, which are, for example, obtained by treatment of pyrogenic silica in the presence of hexamethyidisilazane. Silicas thus treated are named "Silica silylate" according to the CTFA (6$^{th}$ edition, 1995). They are, for example, marketed under the names "Aerosil R812®" by Degussa and "Cab-O-Sil TS-530®" by Cabot.
- dimethylsilyloxyl or polydimethylsiloxane groups, which are, for example, obtained by treatment of pyrogenic silica in the presence of polydimethylsiloxane or dimethyidichlorosilane. Silicas thus treated are named "Silica dimethyl silylate" according to the CTFA (6$^{th}$ edition, 1995). They are, for example, marketed under the names "Aerosil R972®" and "Aerosil R974®" by Degussa and "Cab-O-Sil TS-610®" and "Cab-O-Sil TS-720®" by Cabot.

In one embodiment, the at least one pyrogenic silica displays a particle size ranging from nanometric to micrometric, for example ranging from about 5 to 200 nm.

In one embodiment, the at least one inorganic thickening agent of oils can be present in the composition disclosed herein in an amount ranging from 0.5% to 7% by weight, relative to the total weight of the composition, for example ranging from 1% to 5% by weight or ranging from 1% to 3% by weight.

In another embodiment, the at least one thickening agent of oils is present in the composition disclosed herein in an amount ranging from 0.1 to 20% by weight relative to the total weight of the composition, for example ranging from 0.5 to 15% by weight, or for example ranging from 1 to 10% by weight.

Aqueous Phase

In one embodiment, the composition disclosed herein can comprise an aqueous phase.

The aqueous phase comprises water. In one embodiment, the water can be a floral water, such as cornflower water, and/or a mineral water, such as Vittel water, Lucas water, or La Roche Posay water, and/or a thermal water.

In another embodiment, the aqueous phase can further comprise at least one organic solvent miscible with water (at ambient temperature—25° C.) such as for example:
- polyols comprising, for example, from 2 to 20 carbon atoms, such as from 2 to 10 carbon atoms, or such as from 2 to 6 carbon atoms, such as glycerol, propylene glycol, butylene glycol, pentylene glycol, hexylene glycol, dipropylene glycol, and diethylene glycol;
- glycol ethers (for example comprising from 3 to 16 carbon atoms) such as the ($C_1$-$C_4$) alkyl ethers of mono, di- or tripropylene glycol, the ($C_1$-$C_4$) alkyl ethers of mono, di- or triethylene glycol; and
- mixtures thereof.

In another embodiment, the aqueous phase can further comprise at least one stabilizing agent, for example sodium chloride, magnesium dichloride and/or magnesium sulphate.

In another embodiment, the aqueous phase can also comprise at least one water-soluble or water-dispersible compound compatible with an aqueous phase, such as gelling agents, filmogenic polymers, thickeners, surfactants, and mixtures thereof.

In one embodiment, the aqueous phase can be present in the composition disclosed herein in an amount ranging from 1 to 95% by weight, relative to the total weight of the composition, for example from 3 to 80% by weight, or for example from 5 to 60% by weight.

Powder Phase

In one embodiment, the composition disclosed herein comprises a powder phase, for example chosen from pigments, fillers and/or nacres, and mixtures thereof.

According to one embodiment, the composition disclosed herein can comprise at least one pigment.

As used herein, "pigments" mean inorganic or organic particles, insoluble in the liquid organic phase, intended to color and/or opacify the composition.

In one embodiment, the at least one pigment can be chosen from inorganic and organic pigments. In another embodiment, the at least one pigment is chosen from metal oxides, such as the oxides of iron (for instance those of yellow, red, brown or black colour), titanium dioxides, cerium oxide, zirconium oxide and chromium oxide; manganese violet, ultramarine blue, Prussian blue, ultramarine blue, ferric blue, bismuth oxychloride, nacre, mica coated with titanium or bismuth oxychloride, colored nacre pigments such as titanium mica with iron oxides, titanium mica comprising ferric blue or chromium oxide, titanium mica comprising an organic pigment of the type cited above, and nacre pigments based on bismuth oxychloride, and mixtures thereof.

In one embodiment, at least one pigment chosen from pigments of iron oxides and titanium dioxide is used.

In another embodiment, the at least one pigment can be treated with at least one hydrophobic agent to render it compatible with the organic phase of the composition. In a further embodiment, the at least one hydrophobic treatment agent is chosen from silicones such as the methicones, dimethicones and perfluoroalkylsilanes; fatty acids such as stearic acid; metal soaps such as aluminium dimyristate, the aluminium salt of hydrogenated tallow glutamate, perfluoroalkyl phosphates, perfluoroalkyl silanes, perfluoroalkyl silazanes, hexafluoropropylene polyoxides, polyorganosiloxanes containing perfluoroalkyl groups, perfluoro polyethers, amino acids; N-acylated amino acids or salts thereof; lecithin, isopropyl triisostearyl titanate; and mixtures thereof.

The N-acylated amino acids can comprise an acyl group comprising from 8 to 22 carbon atoms, such as for example a 2-ethyl hexanoyl, caproyl, lauroyl, myristoyl, palmitoyl, stearoyl, or cocoyl group. The salts of these compounds can be chosen from aluminium, magnesium, calcium, zirconium, zinc, sodium and potassium salts. The amino acid can for example be lysine, glutamic acid and alanine.

As used herein, the term alkyl mentioned in the compounds cited above means an alkyl group comprising from 1 to 30 carbon atoms, for example comprising from 5 to 16 carbon atoms.

Examples of hydrophobically treated pigments include, but are not limited to those described in European Patent Application EP-A-1086683.

The at least one pigment can be present in the composition disclosed herein in an amount greater than or equal to 0.01 to 50% by weight, relative to the total weight of the composition, for example ranging from 0.1% to 30% by weight, or for example ranging from 0.5% to 20% by weight, or for example ranging from 0.5% to 15% by weight.

In one embodiment, apart from the at least one pigment, the powder phase of the composition disclosed herein can comprise at least one filler and/or nacre.

According to one embodiment, the composition disclosed herein comprises at least one filler.

As used herein, "fillers" mean particles of any shape, colorless or white, inorganic or synthetic, insoluble in the medium of the composition whatever the temperature at which the composition is manufactured.

The fillers can be inorganic or organic of any shape, platelets, spherical or oblong, whatever the crystallographic form (for example flake, cubic, hexagonal, orthorhombic, etc). Examples of fillers include, but are not limited to, talc, mica, silica, kaolin, polyamide powders (Nylon®), poly-β-alanine powders, polyethylene or polymethyl methacrylate powders, polyurethane powders such as the powder of hexamethylene diisocyanate and trimethylol hexyl lactone copolymer sold under the names Plastic Powder D-400 by Toshiki, tetrafluoroethylene polymer powders (Teflon®), lauroyl-lysine, starch, boron nitride, hollow polymeric microspheres such as those of polyvinylidene chloride/acrylonitrile such as Expancel® (Nobel Industrie), copolymers of acrylic acid, silicone resin powders, such as silsesquioxane powders (silicone resin powders described, for example, in European Patent No. EP 293795; Tospearls® from Toshiba, for example), elastomeric polyorganosiloxane particles, precipitated calcium carbonate, magnesium carbonate and hydrogen carbonate, hydroxyapatite, hollow silica microspheres, glass or ceramic microcapsules, metal soaps derived from organic carboxylic acids comprising from 8 to 22 carbon atoms, such as from 12 to 18 carbon atoms, for example zinc, magnesium or lithium stearate, zinc laurate, magnesium myristate, barium sulphate, and mixtures thereof.

In one embodiment, the at least one filler can be present in the composition disclosed herein in an amount ranging from 0.01% to 99% by weight, relative to the total weight of the composition, for example ranging from 0.02% to 9% by weight, for example ranging from 0.05% to 90% by weight.

In another embodiment, apart from the at least one pigment and the at least one filler, the particulate phase of the composition disclosed herein can comprise at least one nacre.

As used herein, "nacres" mean iridescent particles, such as those produced by certain molluscs in their shell, or else synthesized, which are insoluble in the medium of the composition.

The at least one nacre is chosen from white nacreous pigments, such as mica coated with titanium or bismuth oxychloride; colored nacreous pigments, such as titanium mica with iron oxides; titanium mica, for example with ferric blue or chromium oxide; titanium mica with at least one organic pigment of the precipitated type; and nacreous pigments based on bismuth oxychloride.

The at least one nacre can be present in the composition disclosed herein in an amount ranging from 0.01% to 50% by weight, relative to the total weight of the composition, for example from 0.02% to 30% by weight or from 0.5% to 20% by weight.

Additional Colorants

In another embodiment, the composition disclosed herein can comprise at least one additional colorant chosen from water-soluble and liposoluble colorants.

Examples of water-soluble colorants include, but are not limited to, beetroot juice, methylene blue, and caramel.

As used herein, "liposoluble colorants" mean generally organic compounds soluble in fatty substances, such as oils.

Examples of liposoluble colorants include, but are not limited to Sudan red, D&C Red No. 17, D&C Green No. 6, β-carotene, soya oil, Sudan brown, D&C Yellow No. 11, D&C Violet No. 2, D&C orange No. 5, quinoline yellow, annato, and the bromo acids.

In one embodiment, the at least one additional colorant can be present in the composition disclosed herein in an amount ranging from 0.001% to 30% by weight, relative to the total weight of the composition, for example ranging from 0.01% to 20% by weight or from 0.02% to 10% by weight.

Additional Cosmetic Adjuvants

In one embodiment, the composition disclosed herein can comprise at least one cosmetic adjuvant, which can be chosen, for example, from antioxidants, perfumes, preservatives, neutralizing agents, surfactants, sunscreens, vitamins, hydrating agents, self-tanning compounds, antiwrinkle active substances, emollients, hydrophilic and lipophilic active substances, anti-free radical agents, deodorants, sequestering agents, and filmogenic agents.

Also disclosed herein is a process for making-up and/or caring for the skin comprising applying onto the skin a composition comprising a liquid fatty phase comprising at least one resin of number average molecular weight less than or equal to 10,000 g/mol, chosen from rosin, derivatives of rosin, and hydrocarbon resins; and at least one hydrocarbon block copolymer chosen from styrene-ethylene/propylene and styrene-ethylene/butadiene diblock copolymers, and styrene-ethylene/butadiene-styrene, styrene-isoprene-styrene and styrene-butadiene-styrene triblock copolymers; the composition further comprising at least one fatty substance whose melting point is greater than 25° C., chosen from waxes or pasty fatty substances, the composition comprising less than 5% volatile oil relative to the total weight of the composition, for example less than 2% thereof, such as no volatile oil.

According to one embodiment, the at least one resin of the composition of the make-up and/or care process is chosen from hydrogenated indene/methylstyrene/styrene copolymers.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLES

Examples 1 to 4

Liquid lipsticks disclosed herein having the following general formula were prepared:

| Stage | COMPOSITION | Type | Concentration in weight % |
|---|---|---|---|
| Pregel | ISOPROPYL ISOSTEARATE | FATTY SUBSTANCE | 1.3 |
| Pregel | STYRENE-ETHYLENE/BUTYLENE-STYRENE BLOCK COPOLYMER (KRATON ®) | POLYMER | 7.5 |
| Pregel | HYDROGENATED POLYDECENE (VISCOSITY: 54 CPS) | POLYMER | 10 |
| Pregel | HYDROGENATED POLYISOBUTENE | POLYMER | 18.5 |
| Pregel | HYDROGENATED STYRENE/METHYL STYRENE/INDENE COPOLYMER (REGALITE ® R 1100) | POLYMER | 15 |
| Pregel (half by weight) | 2-OCTYL DODECYL NEOPENTANOATE (QS) | FATTY SUBSTANCE | 26.029 |
| Pregel | FATTY SUBSTANCE OF MELTING POINT GREATER THAN 25° C. | PASTY SUBSTANCE OR WAX | 5 |
|  | N-LAUROYL L-LYSINE | FILLER | 1 |
|  | CALCIUM SALT OF LITHOL RED B | COLORANT | 0.225 |
|  | BROWN AND YELLOW IRON OXIDES (75/25) | COLORANT | 0.255 |

| Stage | COMPOSITION | Type | Concentration in weight % |
|---|---|---|---|
| | POLYBUTENE (MONOOLEFINS/ ISOPARAFFINS 95/5) (MW: 2060) | POLYMER | 10 |
| | HYDROPHOBIC PYROGENIC SILICA, SURFACE-TREATED WITH DIMETHYLSILANE | FILLER | 5 |
| | BLACK IRON OXIDE | COLORANT | 0.041 |
| | RUTILE TITANIUM OXIDE TREATED WITH ALUMINA/SILICA/TRI-METHYOLPROPANE | COLORANT | 0.15 |
| | TOTAL: | | 100 |

Operating Procedure:

Preparation of the pregel:

In a double-walled pan, the block polymer Kraton ® was mixed with the hydrogenated polyisobutene, isopropyl isostearate and half of the 2-octyldodecyl neopentanoate by weight by means of a Rayneri.

This mixture was heated to 100° C. for two hours to obtain a gel transparent and homogeneous at 100° C. Then, still at 100° C., the Regalite was added. The mixture was left for one hour with stirring at 100° C.

The fatty substance with a melting point greater than 25° C. was then added, the mixture still being maintained at 100° C.

The different fatty substances whose melting point is greater than 25° C. used for the creation of the different pregels were:

Example 1 hydrogenated castor oil dimer dilinoleate (Risocast DA-L marketed by Kokyu Alcohol Kogyo) which is a pasty fatty substance.

Example 2 hydrogenated castor oil isostearate (Salacos HCIS(V)-L marketed by Nisshin Oil) which is a pasty fatty substance.

Example 3 bis-diglyceryl polyacyladipate-2 (Softisan 645 marketed by Sasol) which is a pasty fatty substance.

Example 4

PEG-45/dodecyl glycol copolymer (Elfacost ST9 marketed by Azko Nobel) which is a pasty fatty substance.

End of preparation of the composition:

The colorants and the fillers were ground in the other half of the 2-octyldodecyl neopentanoate by weight. This ground material was added, still at 100° C., to the previously prepared pregel. Next, the polybutene was added, then the hydrophobic pyrogenic silica which was dispersed on the Rayneri, still at a temperature of 100° C.

Thus the whole preparation phase was carried out at 100° C. After cooling to ambient temperature, a liquid lipstick was obtained, the deposit whereof was shiny and the sheen thereof was persistent. Moreover, a low level of migration was observed.

Example 5

A liquid lipstick disclosed herein having the following general formula was prepared:

| Stage | COMPOSITION | Type | Concentration in weight % |
|---|---|---|---|
| | N-LAUROYL L-LYSINE | FILLER | 1 |
| Pregel | ESTERS OF PLANT FATTY ACIDS, GLYCERYL ISOSTEARATE AND ADIPATE | PASTY FATTY SUBSTANCE | 9 |
| Pregel | ISOPROPYL ISOSTEARATE | FATTY SUBSTANCE | 2.3 |
| | CALCIUM SALT OF LITHOL RED B | COLORANT | 0.225 |
| | BROWN AND YELLOW IRON OXIDES (75/25) | COLORANT | 0.255 |
| Pregel | HYDROGENATED POLYISOBUTENE | POLYMER | 23.5 |
| Pregel | HYDROGENATED STYRENE/METHYL STYRENE/INDENE COPOLYMER (REGALITE ® R 1100) | POLYMER | 15 |
| | HYDROPHOBIC PYROGENIC SILICA, SURFACE-TREATED WITH DIMETHYLSILANE | FILLER | 5 |
| | POLYBUTENE (MONOOLEFINS/ ISOPARAFFINS 95/5) (MW: 2060) | POLYMER | 12 |
| Pregel | STYRENE-ETHYLENE/BUTYLENE-STYRENE BLOCK COPOLYMER (KRATON ®) | POLYMER | 7.5 |
| | BLACK IRON OXIDE | COLORANT | 0.041 |
| | RUTILE TITANIUM OXIDE TREATED WITH ALUMINA/SILICA/TRI-METHYOLPROPANE | COLORANT | 0.15 |

-continued

| Stage | COMPOSITION | Type | Concentration in weight % |
|---|---|---|---|
| Pregel (half by weight) | 2-OCTYLDODECYL NEOPENTANOATE (QS) | FATTY SUBSTANCE | 24.029 |
| | TOTAL: | | 100 |

Operating Procedure:

The operating procedure used was the same as that described above.

Results

The lipstick was applied on a panel of six women. A very good level of sheen was observed and also persistence of the sheen for at least 4 hours after application.

Examples 1 to 5 thus show that the combination of the hydrogenated styrene/methyl styrene/indene resin copolymer Regalite R 1100, Kraton and a pasty substance in the absence of volatiles makes it possible to obtain a deposit having a good level of sheen and very good persistence of the sheen after application for at least 4 hours.

Example 6

Comparative

A liquid lipstick having the following composition and not comprising a fatty substance whose melting point is greater than 25° C. was prepared:

| Stage | COMPOSITION | Type | Concentration in weight % |
|---|---|---|---|
| | N-LAUROYL L-LYSINE | FILLER | 1 |
| Pregel | ISOPROPYL ISOSTEARATE | FATTY SUBSTANCE | 1.35 |
| | RUTILE TITANIUM OXIDE TREATED WITH ALUMINA/SILICA/TRI-METHYOLPROPANE | COLORANT | 0.15 |
| | BLACK IRON OXIDE | COLORANT | 0.041 |
| Pregel | STYRENE-ETHYLENE/BUTYLENE-STYRENE BLOCK COPOLYMER (KRATON ®) | POLYMER | 7.4 |
| | POLYBUTENE (MONOOLEFINS/ ISOPARAFFINS) (MW: 920) | POLYMER | 15 |
| | HYDROPHOBIC PYROGENIC SILICA, SURFACE-TREATED WITH DIMETHYLSILANE | FILLER | 5 |
| Pregel | HYDROGENATED STYRENE/METHYL STYRENE/INDENE COPOLYMER (REGALITE ® R 1100) | POLYMER | 22.1 |
| Pregel | HYDROGENATED POLYDECENE (MW: 549 — 34% TRIMERIC, 44% TETRAMERIC, 17% PENTAMERIC, 4% HEXAMERIC) | POLYMER | 14 |
| | BROWN AND YELLOW IRON OXIDES (75/25) | COLORANT | 0.255 |
| | CALCIUM SALT OF LITHOL RED B | COLORANT | 0.225 |
| Pregel (half by weight) | 2-OCTYLDODECYL NEOPENTANOATE (QS) | FATTY SUBSTANCE | 33.479 |
| | TOTAL: | | 100 |

The mode of preparation of the composition was the same as in the previous examples.

As in the case of example 5, this lipstick was applied on a panel of six women. The sheen of the deposit and the persistence of the sheen was observed for 4 hours after application.

Comparison of the lipsticks of examples 5 (invention) and 6 (comparative) makes it possible to show that a better persistence of the sheen was obtained in the case of the composition of the example 5 comprising a pasty fatty substance for which no decrease in the level of sheen was observed for at least 4 hours.

Moreover, the composition disclosed herein of example 5 migrated less than the composition of the comparative example 6.

Example 7

A solid lipstick according to the present disclosure herein having the following composition was prepared:

|  | COMPOSITION | Type | Concentration in weight % |
|---|---|---|---|
| Pregel (half by weight) | 2-OCTYLDODECYL NEOPENTANOATE | FATTY SUBSTANCE | 20.6 |
| Pregel | ESTERS OF PLANT FATTY ACIDS, GLYCERYL ISOSTEARATE AND ADIPATE | PASTY FATTY SUBSTANCE | 7.1 |
| Pregel | ISOPROPYL ISOSTEARATE | FATTY SUBSTANCE | 6.55 |
|  | RUTILE TITANIUM OXIDE TREATED WITH ALUMINA/SILICA/TRI-METHYOLPROPANE | COLORANT | 0.2 |
|  | CALCIUM SALT OF LITHOL RED B | COLORANT | 0.45 |
|  | ALUMINIUM LAKE OF BRILLIANT BLUE FCF ON ALUMINA (12/88) | COLORANT | 0.2 |
|  | BROWN AND YELLOW IRON OXIDES (75/25) | COLORANT | 0.95 |
| Pregel | ETHYLENE HOMOPOLYMER | WAX | 4.92 |
| Pregel | HYDROGENATED STYRENE/METHYL STYRENE/INDENE COPOLYMER (REGALITE ® R 1100) | POLYMER | 15 |
| Pregel | MIXTURE OF LINEAR LONG-CHAIN FATTY ACID (C30-C50) AND HYDROCARBON WITH SAME NUMBER OF CARBONS (80/20) | WAX | 0.5 |
| Pregel | POLYETHYLENE WAX (MW: 500) | WAX | 5.88 |
|  | ALUMINIUM LAKE OF TARTRAZINE ON ALUMINA (15/85) | COLORANT | 0.85 |
|  | MICA-TITANIUM OXIDE (59/41) | NACRE | 2.8 |
|  | MICA-TITANIUM OXIDE (52/48) | NACRE | 1 |
|  | MICA-TITANIUM OXIDE (60/40) | NACRE | 0.5 |
| Pregel | STYRENE-ETHYLENE/BUTYLENE-STYRENE BLOCK COPOLYMER (KRATON ®) | POLYMER | 7.5 |
| Pregel (half by weight) | HYDROGENATED POLYISOBUTENE (QS) | POLYMER | 25 |
|  | TOTAL: |  | 100 |

Operating Procedure

Preparation of pregel:

In a double-walled pan, the Kraton ® block polymer was mixed with half of the hydrogenated polyisobutene by weight, the isopropyl isostearate and half of the 2-octyidodecyl neopentanoate by weight by means of a Rayneri.

This mixture was heated at 100° C. for two hours to obtain a gel transparent and homogeneous at 100° C. Then, still at 100° C., the Regalite is added. The mixture was left for one hour with stirring at 100° C.

Next, the fatty substances with a melting point greater than 25° C., namely the pasty fatty substance and the three different waxes, were added, the mixture still being maintained at 100° C.

End of the preparation of the composition:

The colorants were ground in the other half of the 2-octyldodecyl neopentanoate by weight and hydrogenated polyisobutene. This ground product was added, still at 100° C., to the previously prepared pregel. Next, the nacres were added, still at a temperature of 100° C.

Thus the whole preparation phase was carried out at 100° C. The lipstick was then poured into a mold and allowed to cool for 24 hours at 20° C. A stick of the composition having a circular cross section 12.7 mm in diameter was thus prepared.

The stick thus obtained made it possible to obtain a homogeneous, shiny deposit, whose sheen was persistent. Further, a low level of migration was observed.

What is claimed is:

1. A composition for make-up and/or care of the skin comprising a fatty phase comprising:

at least one hydrocarbon resin of number average molecular weight less than or equal to 10,000 g/mol, chosen from indene hydrocarbon resins, aliphatic pentadiene resins, mixed pentadiene and indene resins, diene resins of cyclopentadiene dimers, and diene resins of isopropene dimers;

at least one hydrocarbon block copolymer, chosen from sequenced copolymers, optionally hydrogenated, comprising at least one styrene block and at least one block comprising units chosen from butadiene, ethylene, propylene, butylene, and isoprene, wherein the at least one hydrocarbon block copolymer is present in the composition in an amount ranging from 0.1% to 15% by weight, relative to the total weight of the composition;

at least one fatty substance whose melting point is greater than 25° C., chosen from waxes and pasty fatty substances, wherein the at least one fatty substance whose melting point is greater than 25° C. is present in the composition in an amount ranging from 0.1 to 20% by weight, relative to the total weight of the composition;

said composition comprising less than 5% by weight of volatile oil relative to the total weight of the composition.

2. A composition according to claim 1, wherein said composition comprises less than 10% of water by weight relative to the total weight of the composition.

3. A composition according to claim 1, wherein said composition comprises less than 10% by weight of silicone compound, relative to the total weight of the composition.

4. A composition according to claim 1, wherein said composition is in liquid form at ambient temperature (25° C.).

5. A composition according to claim 1, wherein said composition is in solid form at ambient temperature (25° C.).

6. A composition according to claim 5, wherein said composition displays a hardness greater than 30 g.

7. A composition according to claim 1, wherein the at least one fatty substance whose melting point is greater than 25° C. comprises at least one wax and at least one pasty fatty substance.

8. A composition according claim 1, wherein the at least one resin displays a number average molecular weight ranging from 250 to 10,000 g/mol.

9. A composition according to claim 8, wherein the at least one resin displays a number average molecular weight less than or equal to 5,000 g/mol.

10. A composition according to claim 1, wherein the at least one resin is an indene hydrocarbon resin derived from the polymerization of at least one indene monomer and at least one monomer chosen from styrene, methylindene, and methylstyrene.

11. A composition according to claim 10, wherein the at least one indene hydrocarbon resin is hydrogenated.

12. A composition according to claim 11, wherein the at least one resin is an indene resin chosen from hydrogenated indene/methylstyrene/styrene copolymers.

13. A composition according to claim 1, wherein the at least one resin is an aliphatic pentadiene resin derived from the polymerization of the monomer 1,3-pentadiene (trans or cis piperylene) and at least one monomer chosen from isoprene, butene, 2-methyl-2-butene, pentene, and 1,4-pentadiene.

14. A composition according to claim 11, wherein the at least one resin is a mixed pentadiene and indene resin.

15. A composition according to claim 11, wherein the at least one resin is a diene resin of cyclopentadiene dimers derived from the polymerization of a first monomer chosen from indene and styrene, and a second monomer chosen from the dimers of cyclopentadiene.

16. A composition according to claim 11, wherein the at least one resin is a diene resin of isoprene dimers derived from the polymerization of at least one monomer chosen from α-pinene, β-pinene, and limonene.

17. A composition according to claim 1, wherein the at least one resin is present in an amount ranging from 0.1 to 30% by weight, relative to the total weight of the composition.

18. A composition according to claim 1, wherein the at least one wax is chosen from:
hydrocarbon waxes;
waxes obtained by catalytic hydrogenation of animal and/or plant oils comprising linear and/or branched $C_8$-$C_{32}$ fatty chains;
hydrogenated oils set at 25° C.;
silicone waxes; and
fluorinated waxes.

19. A composition according to claim 1, wherein the at least one pasty fatty substance is chosen from:
lanoline and derivatives thereof;
polyol ethers chosen from ethers of pentaerythritol and polyalkylene glycol, and ethers of fatty alcohol and sugar;
silicone compounds whether or not polymeric;
fluorinated compounds whether or not polymeric;
vinyl polymers;
liposoluble polyethers resulting from polyetherification between one or more from C2-C100 diols; and
esters.

20. A composition according to claim 1, further comprising at least one nonvolatile oil.

21. A composition according to claim 20, wherein the at least one nonvolatile oil is present in the composition in an amount ranging from 10% to 90% by weight, relative to the total weight of the composition.

22. A composition according to claim 1, wherein the fatty phase of the composition is present in the composition in a total amount ranging from 10% to 95% by weight, relative to the total weight of the composition.

23. A composition according to claim 1, wherein the at least one hydrocarbon block copolymer is an amorphous copolymer formed by polymerization of ethylenic carbide monomers, comprising one or two ethylenic unsaturations, and comprising from 2 to 5 carbon atoms.

24. A composition according to claim 23, wherein the at least one hydrocarbon block copolymer is formed by polymerization of an olefin chosen from ethylene, propylene, butadiene and isoprene.

25. A composition according to claim 24, wherein the at least one hydrocarbon block copolymer is a copolymer, which may be optionally hydrogenated, comprising styrene blocks and C3-C4 ethylene/alkylene blocks.

26. A composition according to claim 25, wherein the at least one hydrocarbon block copolymer is chosen from: optionally hydrogenated diblock copolymers of styrene-ethylene/propylene, styrene-ethylene/butadiene, and styrene-ethylene/butylene; and optionally hydrogenated triblock copolymers of styrene-ethylene/butadiene-styrene, styrene-butylene/ethylene-styrene, styrene-isoprene-styrene and styrene-butadiene-styrene.

27. A composition according to claim 26, wherein the at least one hydrocarbon block copolymer is a mixture of at least one hydrogenated styrene-butylene/ethylene-styrene triblock copolymer and at least one styrene-ethylene/butylene diblock copolymer.

28. A composition according to claim 1, wherein the ratio by weight of the at least one resin to the at least one hydrocarbon block copolymer ranges from 1/1 to 4/1.

29. A composition according to claim 28, wherein the ratio by weight of the at least one resin to the at least one hydrocarbon block copolymer ranges from 1/1 to 3.5/1.

30. A composition according to claim 1, wherein the composition further comprises at least one powder phase chosen from pigments and nacres.

31. A composition according to claim 1, wherein the composition further comprises an aqueous phase in an amount ranging from 3% to 80% by weight relative to the total weight of the composition.

32. A composition according to claim 1, wherein the composition further comprises at least one cosmetic adjuvant chosen from antioxidants, perfumes, preservatives, neutralizing agents, surfactants, sunscreens, vitamins, hydrating agents, self-tanning compounds, antiwrinkle active substances, emollients, hydrophilic and lipophilic active substances, anti-free radical agents, sequestering agents, deodorants, and filmogenic agents.

33. A non-therapeutic procedure for making-up and/or caring for the skin comprising applying onto the skin a composition comprising a fatty phase, comprising:
at least one hydrocarbon resin of number average molecular weight less than or equal to 10,000 g/mol, chosen from indene hydrocarbon resins, aliphatic pentadiene resins, mixed pentadiene and indene resins, diene resins of cyclopentadiene dimers, and diene resins of isopropene dimers;

at least one hydrocarbon block copolymer, chosen from sequenced copolymers, optionally hydrogenated, comprising at least one styrene block and at least one block comprising units chosen from butadiene, ethylene, propylene, butylene, and isoprene, wherein the at least one hydrocarbon block copolymer is present in the composition in an amount ranging from 0.1% to 15% by weight, relative to the total weight of the composition;

at least one fatty substance whose melting point is greater than 25° C. chosen from waxes and pasty fatty substances wherein the at least one fatty substance whose melting point is greater than 25° C. is present in the composition in an amount ranging from 0.1 to 20% by weight, relative to the total weight of the composition;

said composition comprising less than 5% by weight of volatile oil relative to the total weight of the composition.

34. A composition according to claim 1, wherein said composition comprises no volatile oil.

* * * * *